United States Patent [19]
Bria

[11] Patent Number: 5,857,270
[45] Date of Patent: Jan. 12, 1999

[54] OPEN BURNER PLENUM FOR A FLOTATION DRYER

[75] Inventor: Michael P. Bria, Green Bay, Wis.

[73] Assignee: Megtec Systems, Inc., DePere, Wis.

[21] Appl. No.: 846,992

[22] Filed: Apr. 30, 1997

[51] Int. Cl.⁶ ..................................................... F26B 9/00
[52] U.S. Cl. .............................................. 34/629; 34/643
[58] Field of Search ........................... 34/621, 629, 641, 34/643

[56] References Cited

U.S. PATENT DOCUMENTS

| | | | |
|---|---|---|---|
| 3,308,555 | 3/1967 | Kruger | 34/629 |
| 3,739,491 | 6/1973 | Creapo et al. | 34/156 |
| 5,608,973 | 3/1997 | Karlstedt et al. | 34/643 |

*Primary Examiner*—Ronald C. Capassela
*Attorney, Agent, or Firm*—Mitchell D. Bittman; Kevin S. Lemack

[57] ABSTRACT

Air flotation dryer for floatingly drying travelling webs. The dryer includes a housing having a web inlet and a web outlet spaced from the web inlet, and a plurality of elongated air nozzles arranged transversely to the direction of movement of the web and preferably located on opposite sides of the web, the nozzles being secured directly to, supported by and in air-receiving communication with longitudinally extending supply air ducts. An air supply fan is in communication with the supply air ducts to supply air to the nozzles. Heat is provided to the apparatus with a draw-through style burner, which fires into the dryer enclosure and the proper amount of air flow to be heated by the burner (e.g., flowing past the burner) is regulated such as by a return air screen having a predetermined or variable open area, resulting in a simpler design and a lower pressure drop than in the conventional ducted design where the recirculation air is first collected in a duct and is then heated and sent to the supply fan inlet.

24 Claims, 11 Drawing Sheets

TEMPERATURE MEASUREMENTS FOR MAXON OVENPAK
BURNER WITH NO FAN RETURN AIR SCREENS

| | |
|---|---|
| 771 F | 588 F |
| 1093 F | 1240 F |
| 1114 F | 1393 F |
| 1044 F | 1384 F |
| 1056 F | 1475 F |
| 1447 F | 1387 F |
| 1027 F | 992 F |
| 412 F | 431 F |
| 316 F | 401 F |

FAN INLET SCREEN
TEMPERATURES

FAN INLET CONE
TEMPERATURES

NOTE: STEADY STATE CONDITIONS, 400 F
AIR TEMPERATURE SETPOINT.

FIG. 6

TEMPERATURE MEASUREMENTS FOR MAXON OVENPAK
BURNER WITH ALL RETURN AIR PAST BURNER

| 366 F | 357 F |
|-------|-------|
| 499 F | 500 F |
| ----  | 506 F |
| 460 F | 458 F |
| 413 F | 431 F |
| ----  | 453 F |
| 395 F | 413 F |
| 380 F | 405 F |
| 369 F | 371 F |

FAN INLET SCREEN
TEMPERATURES

FAN INLET CONE
TEMPERATURES

NOTE: STEADY STATE CONDITIONS, 400 F
AIR TEMPERATURE SETPOINT.

FIG. 7

TEMPERATURE MEASUREMENTS FOR MAXON OVENPAK
BUMPER WITH INITIAL FAN RETURN AIR SCREEN DESIGN

| 420 F | 374 F |
|---|---|
| 675 F | 560 F |
| 686 F | 744 F |
| 580 F | 686 F |
| 529 F | 597 F |
| 471 F | 382 F |
| 401 F | 312 F |
| 307 F | 324 F |
| 333 F | 375 F |

FAN INLET SCREEN
TEMPERATURES

FAN INLET CONE
TEMPERATURES

NOTE: STEADY STATE CONDITIONS, 400 F
AIR TEMPERATURE SETPOINT.

OPEN BURNER PLENUM FOR A FLOTATION DRYER

BACKGROUND OF THE INVENTION

The present invention relates to web supporting and drying apparatus. In drying a moving web of material, such as paper, film or other sheet or planar material, it is often desirable that the web be contactless supported during the drying operation, in order to avoid damage to the web itself or to any ink or coating on the web surface or surfaces. A conventional arrangement for contactlessly supporting and drying a moving web includes upper and lower sets of air bars extending along a substantially horizontal stretch of the web. Heated air issuing from the air bars floatingly supports the web in a substantially sinusoidal path and expedites web drying. The air bar array is typically inside a dryer housing which can be maintained at a slightly sub-atmospheric pressure by an exhaust blower that draws off the volatiles emanating from the web as a result of the drying of the ink or coating thereon.

U.S. Pat. No. 3,739,491 discloses a high velocity air flotation dryer for drying a running web along the lines of the foregoing. A plurality of spaced air nozzles are positioned on opposite sides of the web. Heated air issuing from the impingement nozzles impinges on the running web to floatingly support and dry the web. The nozzles are in air-receiving communication with an air supply fan through suitable ducting. A burner is located in the ducting downstream from the supply fan outlet for heating the supply air which flows through the air nozzles and impinges on the web. The burner employed is a blow-through type, in that it is located on the outlet or pressure side of the supply air fan. As a result, in order to supply combustion air to the burner, a fan or blower which has a higher pressure output than the supply air fan is required, which can be expensive.

In conventional designs where a draw-through style burner is used, a duct or large plenum collects the return air, and the burner fires into that duct or plenum to heat the air. The duct or plenum is in communication with the inlet of the supply air fan, and supplies the thus heated return air to the fan. Such an arrangement necessarily sends all of the return air past the burner, and is not efficient.

It is therefore an object of the present invention to reduce dryer cost by eliminating ducting otherwise necessary for burner operation. Reduced ductwork also decreases the supply fan pressure requirement which reduces motor size and energy usage.

It is a further object of the present invention to provide a draw-through style burner which fires directly into the dryer enclosure.

It is a still further object of the present invention to regulate the amount of air subjected to the burner flame.

SUMMARY OF THE INVENTION

The problems of the prior art have been overcome by the present invention, which provides an air flotation dryer for floatingly drying travelling webs. The dryer includes a housing having a web inlet and a web outlet spaced from the web inlet, and a plurality of elongated air nozzles arranged transversely to the direction of movement of the web and preferably located on opposite sides of the web, the nozzles being secured directly to, supported by and in air-receiving communication with longitudinally extending supply air ducts. An air supply fan is in communication with the supply air ducts to supply air to the nozzles. Heat is provided to the apparatus with a draw-through style burner, which fires into the dryer enclosure and the proper amount of air flow to be heated by the burner (e.g., flowing past the burner) is regulated such as by a return air screen having a predetermined or variable open area, resulting in a simpler design and a lower pressure drop than in the conventional ducted design where the recirculation air is first collected in a duct and is then heated and sent to the supply fan inlet.

DETAILED DESCRIPTION OF THE INVENTION

Figure 1:
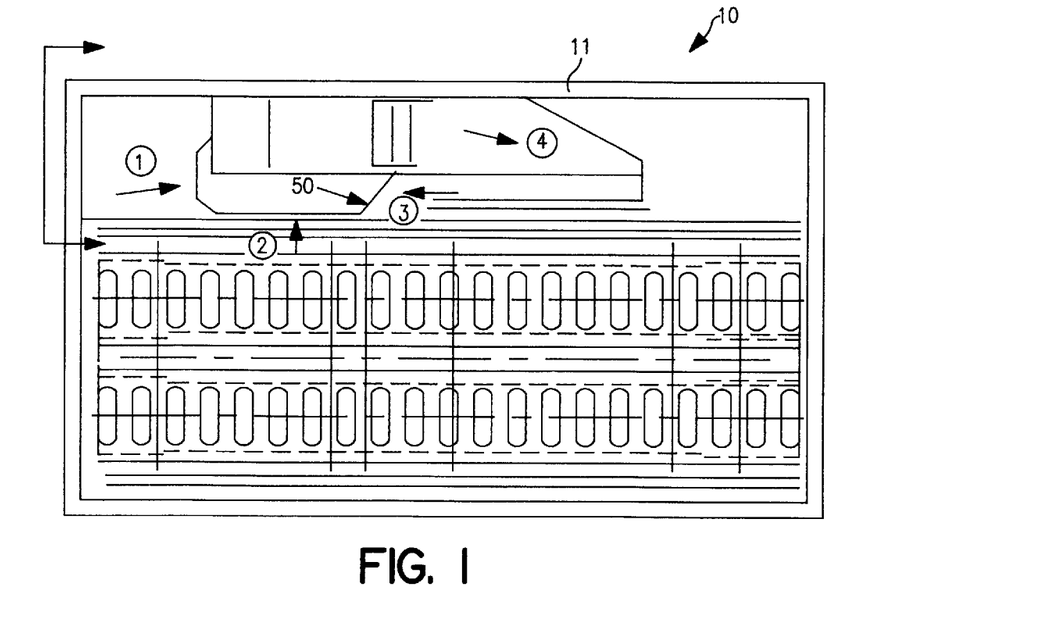
FIG. 1 is a top view of the flotation dryer in accordance with the present invention.
Figure 9:
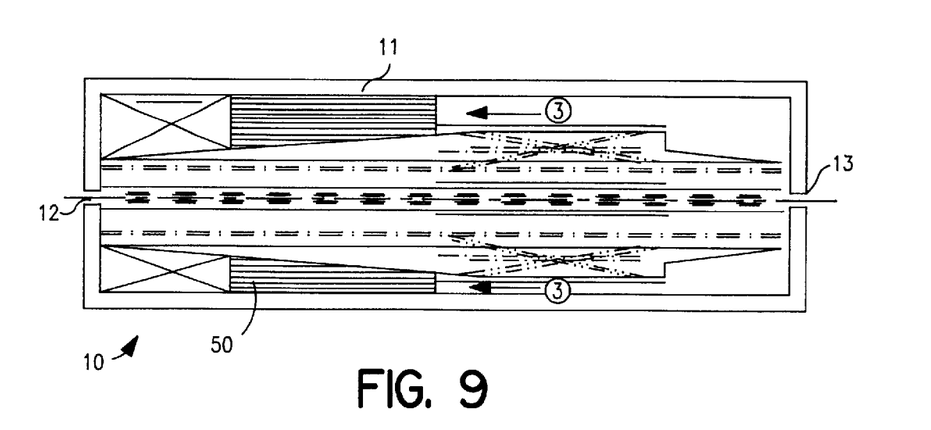
FIG. 9 is a front view of the flotation dryer in accordance with the present invention.
Figure 10:
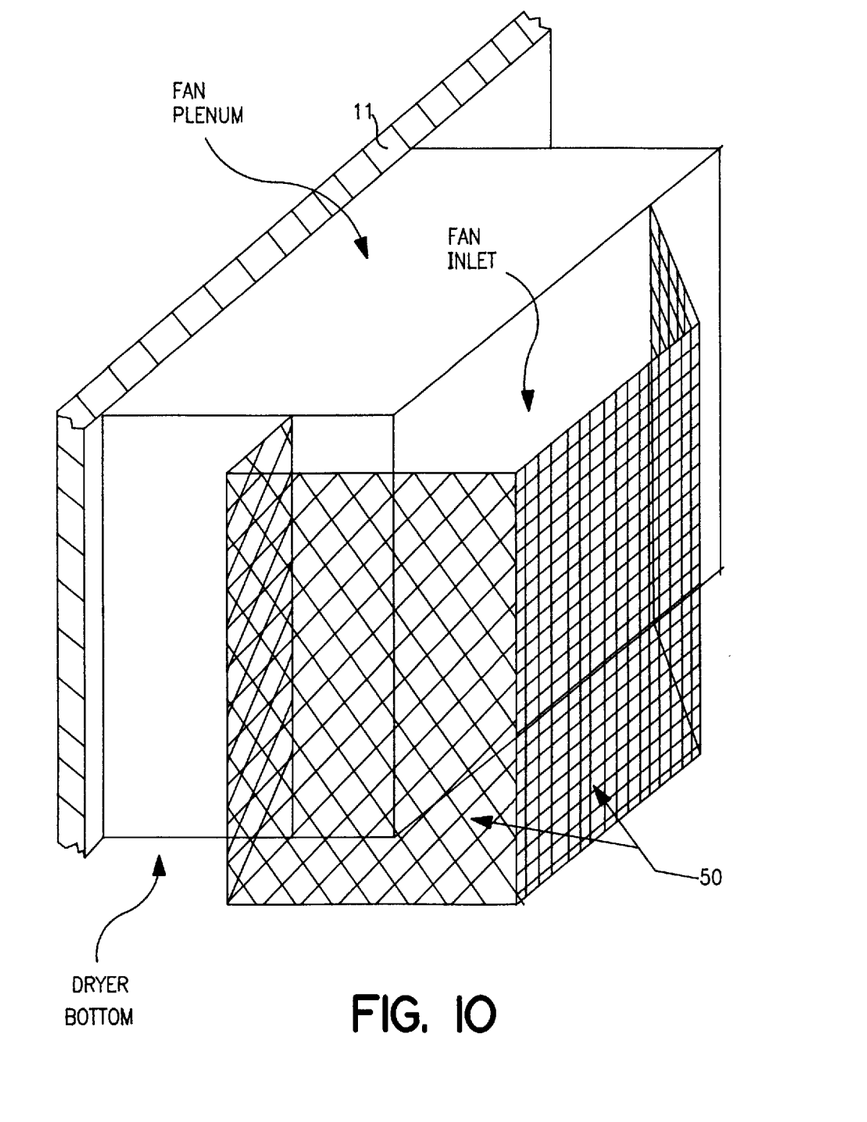
FIG. 10 is an isometric view of the flotation dryer in accordance with the present invention.

Turning first to FIGS. 1, 9 and 10, there is shown generally at 10 a floatation dryer in accordance with the present invention. The dryer 10 is defined by a housing 11 having a web W inlet 12 and web W outlet 13 spaced from the inlet 12. The housing 11 can be constructed of any suitable material, such as steel, and preferably is insulated. A plurality of spaced air nozzles, which can include HI-FLOAT® air bars commercially available from Grace Tec Systems, are arranged above and below the path of the web in air receiving communication with air supply ducts. Heated air emitted from the air nozzles both floats and drys the running web. Means for heating the air preferably comprises a draw-through style burner associated with the dryer housing at 100, and in communication with the supply air fan inlet. A combustion blower may be used in connection with the burner if necessary, and if used, need only operate at a lower pressure, typically 3–4" wg. No collection duct or plenum for the air returning to the supply fan is necessary. The burner heats a portion of the recirculation air prior to its entry into the supply air fan inlet.

Located in the path of air entering the fan inlet is air flow resistance means for inhibiting or obstructing the flow of air, preferably a return air screen 50. The air flow resistance means serves at least two functions. First, it helps prevent debris from entering the supply air stream. Second, it regulates the flow of air past the burner so that the optimum amount of air is heated prior to entering the supply fan inlet. The importance of regulating the amount of air heated by the burner is due to the need to keep air temperatures in the dryer below a certain level. This maximum dryer temperature may be due to limits resulting from the type of material of construction and/or limits due to process constraints. A typical process constraint may require that an air stream containing a particular solvent be kept below a set temperature to prevent the solvent from forming undesired by-products in the air stream. Too little air reaching the burner will cause high temperatures in the dryer. Conversely, sending all the air past the burner is not efficient (a ducted system has this arrangement). Such an arrangement requires more space and/or more energy.

The drying process will dictate the amount of heat input and make-up air necessary for the dryer to operate effectively and safely. Based upon this information, the amount of air flowing past the burner can be determined so that the mixed air temperature, make-up and recirculation air streams will be acceptable for the process and dryer materials. The configuration of the air flow resistance means such as a return air screen 50, in particular, the open area of air flow resistance means, is designed based upon these parameters, bearing in mind that too much open area might not provide a durable enough design, and too small an open area would increase system pressure drop and lower dryer efficiency. In all cases, resistance means with particular total and open areas can be replaced with resistance means of some other total and open areas which will have equal pressure drop if the total area ratio of the two designs is related by the following equation:

$$A_1/A_2 = (K_2/K_1)^{1/2}$$

where $K_2$ and $K_1$ are loss coefficients of the resistance means and depend on the open area thereof.

The burner is exposed to make-up air and only the amount of recirculation air required for the system to operate efficiently and keep air temperatures to some maximum value. Management of air flow is thus effectively accomplished.

Referring again to FIG. 1, the flow of air to and from the supply air fan is shown as arrows numbered 1 through 4. Only flow 1 is heated by the burner flame. In the embodiment shown, the open area of the screen 50 which each air flow encounters is set to a value which will allow sufficient flow in path 1 (past the burner) to keep the air temperature in flow 1 at some desired value, so that the temperature in the dryer is kept at some desired value. (Path 4 is the total outlet of air from the fan.)

For example, assume for a given process that an average temperature of 600° F. is desired in flow 1 at a nominal burner firing rate to minimize the formation of undesired combustion by-products in the recirculating air stream. For a supply air fan outlet temperature of 500° F., make-up air flow of 1990 scfm, supply air flow of 16,500 acfm, and a return air temperature of 420° F., it was found that the amount of air flowing past the burner is large relative to the amount of air returning to the fan from the other directions (flow paths 2 and 3). Accordingly, path 1 needs high open area to minimize pressure drop. Typically 50 to 75% open area is suitable. For this application, 56% is the preferred open area. In the other paths, 2 and 3, less flow is needed so that a more restrictive air flow resistance means (e.g., a screen with less open area) is desired to equalize the pressure drop in these paths. Typically, this screen would be 10–50% open area, more preferably 15 to 40% open area. For this application, an open area of 30% is most preferred for this screen. This determination is made by first calculating the flow needed in the stream past the burner, and then calculating the pressure drops through the parallel flow paths. The open area of each screen is adjusted until the parallel flow paths have equal or substantially equal pressure drop for the desired flow rates.

Those skilled in the art will recognize that other means for regulating the flow of air to the burner and/or directly to the supply fan inlet could be used. For example, a separate filtering screen and a separate flow control screen or screens could be used, or one or more dampers could be used to control the air flow.

Figure 11:
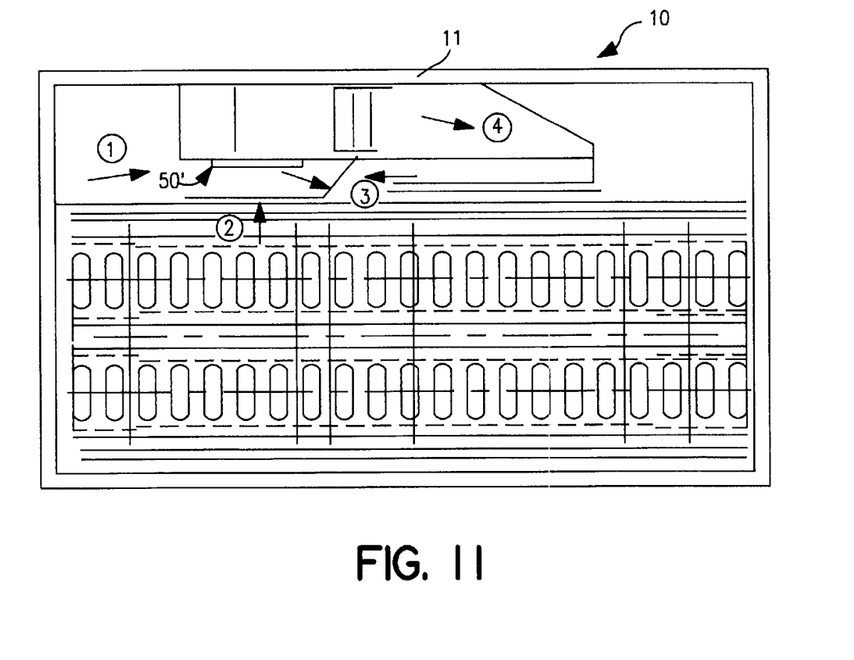
FIG. 11 is a top view of the flotation dryer in accordance with an alternative embodiment of the present invention.
Figure 12:
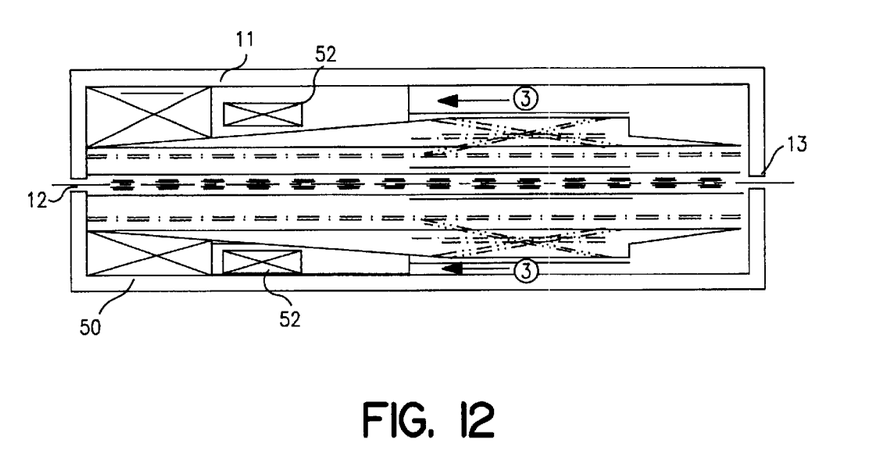
FIG. 12 is a front view of the flotation dryer in accordance with an alternative embodiment of the present invention.
Figure 13A:
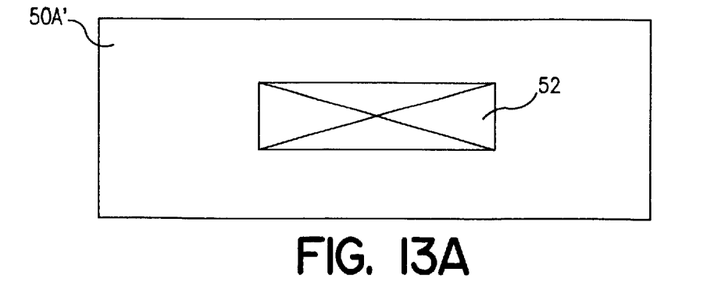
FIG. 13A is a schematic view of an air flow resistance panel having a single opening in accordance with an alternative embodiment of the present invention.
Figure 13B:
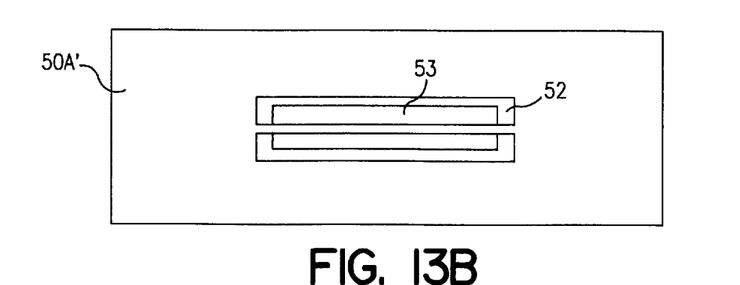
FIG. 13B is a schematic view of an air flow resistance panel having a single adjustable opening in accordance with an alternative embodiment of the present invention.
Figure 13C:
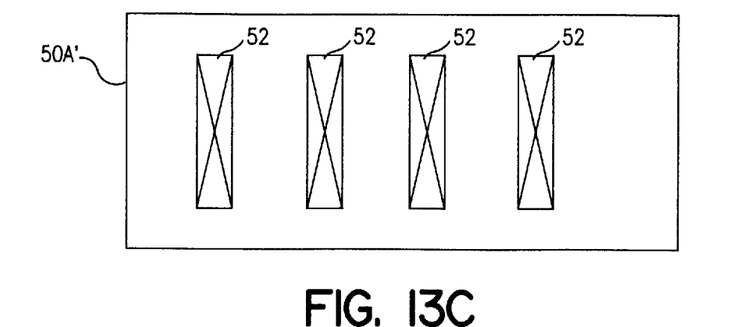
FIG. 13C is a schematic view of an air flow resistance panel having multiple openings in accordance with an alternative embodiment of the present invention.
Figure 13D:
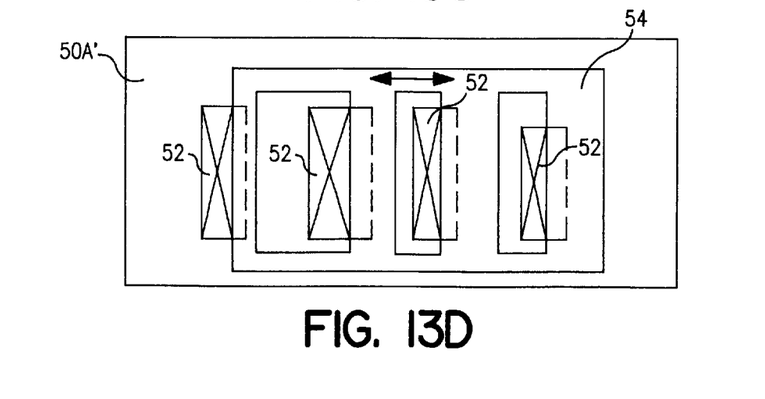
FIG. 13D is a schematic view of an air flow resistance panel having multiple adjustable openings in accordance with an alternative embodiment of the present invention.

An alternative design is shown in FIGS. 11 and 12. A supply fan inlet screens 50' is positioned at the supply fan inlet as shown, and acts as a filtering screen. The air flow resistance means comprises panel 50A' having one or more cut-outs or apertures to control air flow in flow paths 2 and 3 as shown. Various configurations of the cut-outs can be used, as detailed in FIGS. 13A, 13B, 13C and 13D. For example, FIG. 13A depicts a panel 50A' having a single, non-adjustable cut-out 52. FIG. 13B shows a panel 50A' having a single cut-out 52 with a damper 53 associated therewith in order to vary the flow resistance. FIG. 13C shows a panel 50A' having multiple non-adjustable cut-outs 52 (four shown). This embodiment prevents a concentration of air from occurring. A concentration of air may be deleterious to web handling in the dryer. FIG. 13D shows a panel 50A' having multiple cut-outs 52 that are adjustable such as by means of a moveable plate 54 in order to vary the flow resistance.

The cut-out or cut-outs in the panels are preferably 10–50% of the panel areas, most preferably about 30%. The use of such panels to control air flow results in a reduced possibility of the apparatus becoming plugged with debris, thereby resulting in less maintenance. Also, the ease of adjustability of flow resistance with the embodiments such as those shown in FIGS. 13B and 13D is advantageous. Specifically, for many applications, a fixed screen or panel flow resistance which is calculated for some typical operating condition will be acceptable. However, the advantage of having a variable flow resistance would occur in situations where the process conditions change frequently, perhaps because different solvents are removed for different coatings applied to the web being dried. Different solvents might require varying exhaust and make-up air rates and/or maximum process air temperatures. These might require that more or less air flow be heated by (e.g., flow past) the burner and that the flow resistance of the other path to the supply fan change. Also, rather than re-design the return air panels for different dryer sizes such as wider webs or longer zone lengths, it may be easier to use one panel design wherein the flow resistance is variable. This design is then adjusted to work acceptably for each dryer size and operating conditions.

Figure 2:
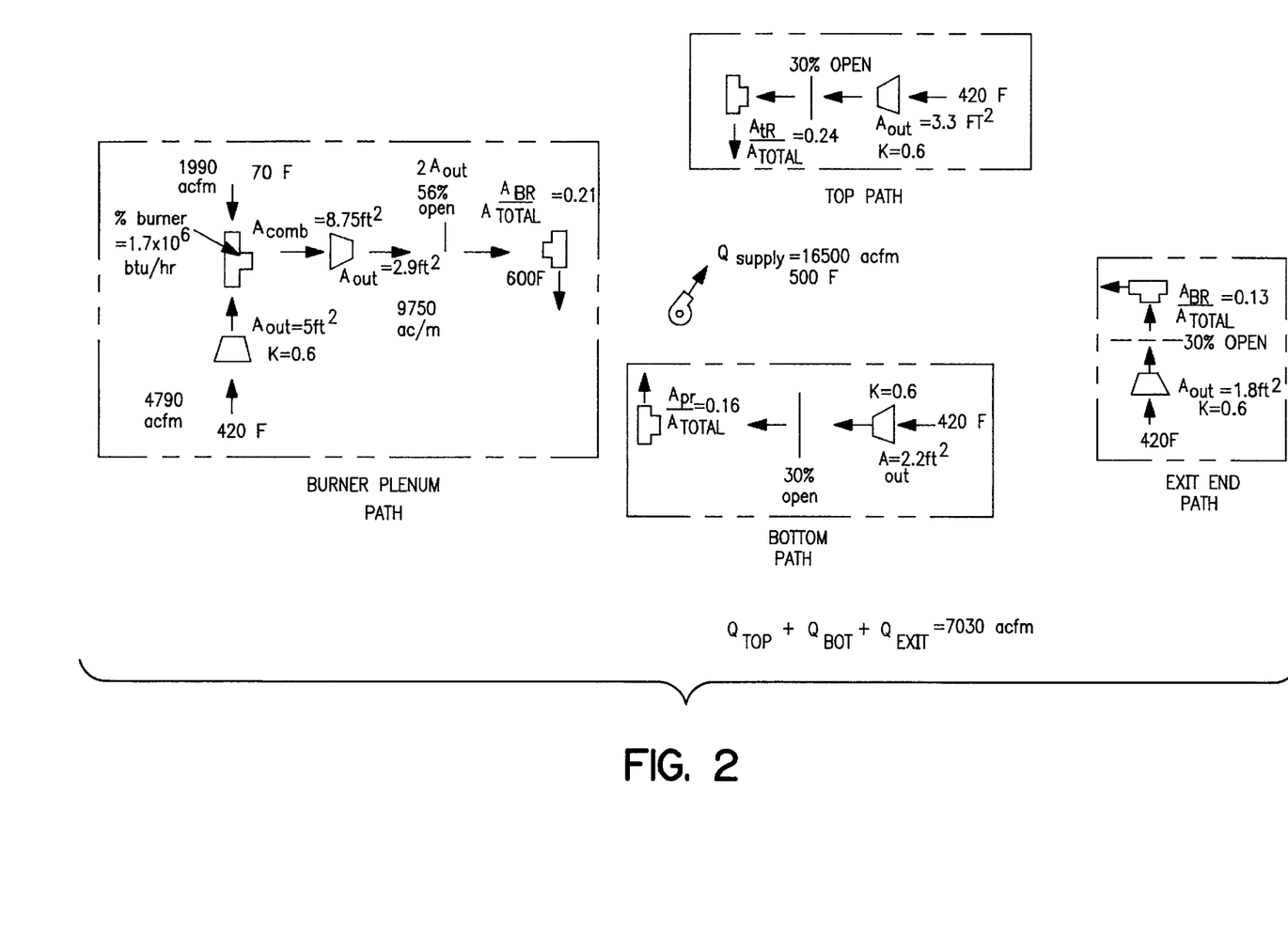
FIG. 2 is a burner plenum/fan inlet flow scheme.

FIG. 2 illustrates the method used to calculate the appropriate open area of the air flow resistance means for each parallel flow path back to the supply fan in the following examples. The air volume for each path will be that value that causes each path to have equal or substantially equal pressure drop. The schematic illustrates the main source of pressure drop in each path.

Slow moving air is accelerated through a small opening of area=$A_{out}$. For the area ratio ($A_{in}/A_{out}$) normally found in this situation, the loss coefficient K is 0.6. Eventually, all of the parallel air flows must combine at the fan inlet. For combining flows, the loss coefficient K depends on the ratios of the areas of the inlet leg and the outlet ($A_{BR}/A_{total}$) and the flow ratio of inlet flow to outlet flow ($A_{BR}/Q_{total}$).

Normally, the drying process will determine the amount of heat input and make-up air necessary for the dryer to operate effectively and safely. Then the amount of air being heated by the burner (e.g., flowing past the burner) can be determined so that the mixed air temperature, make-up and recirculation air streams, will be acceptable for the process and dryer materials. Next, the remaining recirculation air is assumed to flow back to the fan by the alternate parallel flow paths. The open area of the screen for each path can now be estimated through an iterative process such that the strength of the screen and filtering characteristics of the screen are adequate, and the pressure drop is acceptable (small open areas would increase system pressure drop and lower dryer efficiency). When all of the flow paths have equal or substantially equal pressure drop for the assumed flow rates, the design is complete.

COMPARATIVE EXAMPLE 1

Figure 3:
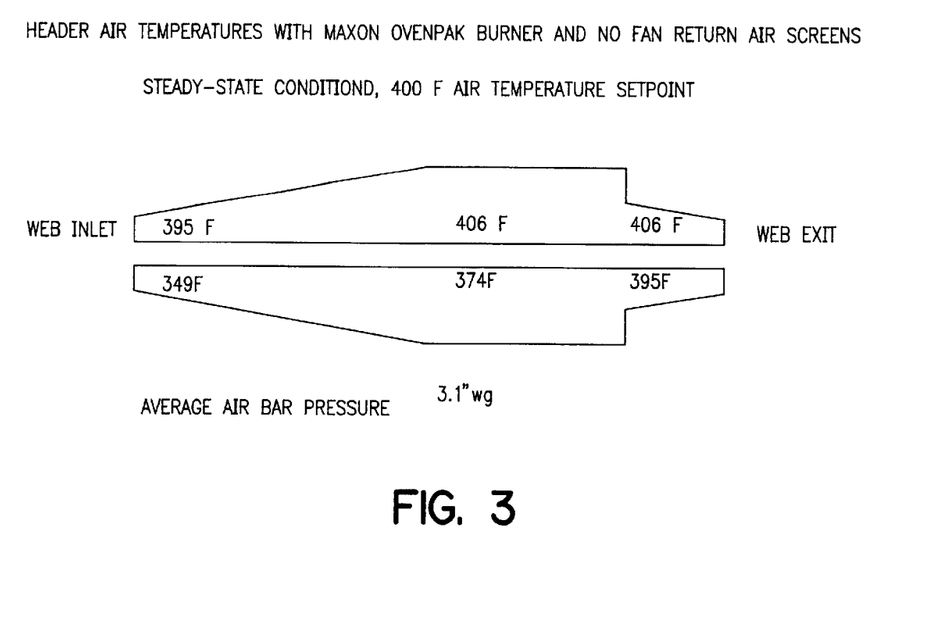
FIG. 3 is an illustration showing header air bar temperatures with no fan return air screens.

For purposes of comparison, header supply air temperatures were measured in a dryer having no return air screen or other means to regulate air flow, and the location of measurement and results are shown in FIG. 3. This illustrates that the non-uniformity of air flow and temperature at the fan inlet due to the absence of the air screen leads to poor uniformity in supply air temperature to the air bars.

Figure 6:
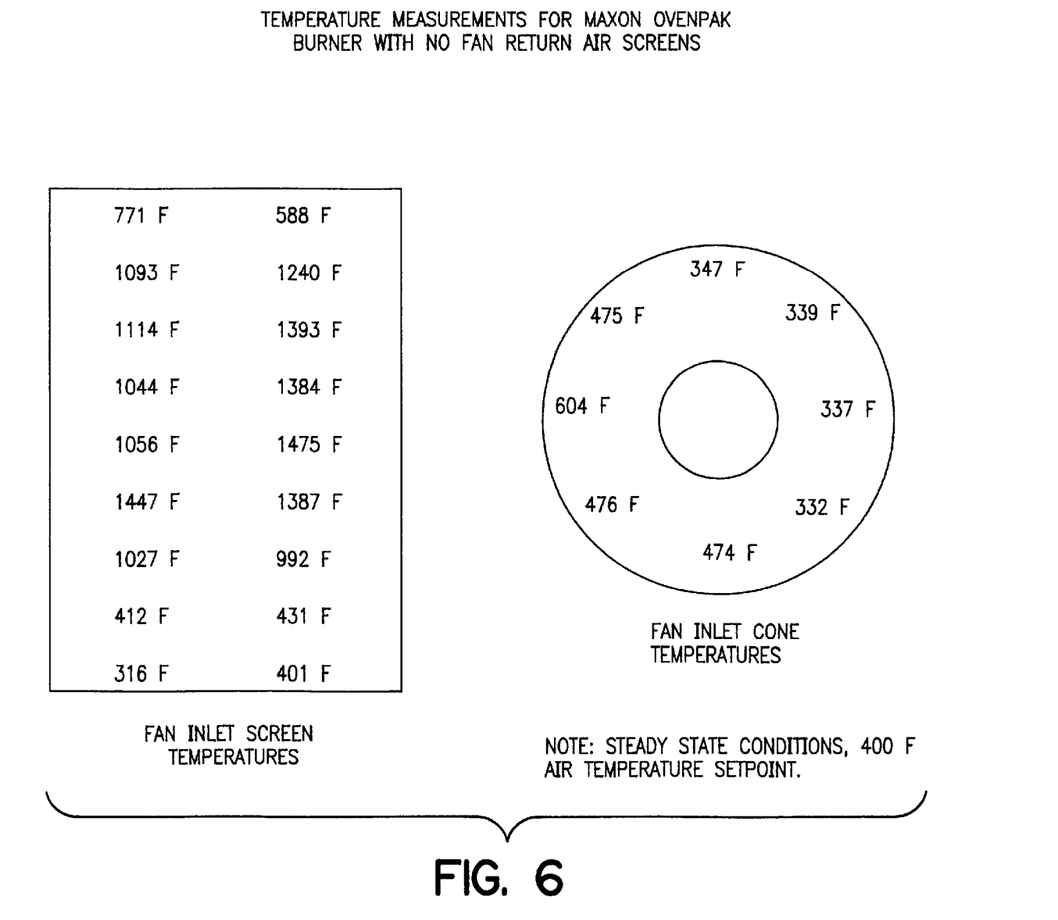
FIG. 6 is an illustration showing temperature measurements at the fan inlet screen and fan inlet cone with no fan return air screen.

Temperature was also measured at the fan inlet cone, at eight 45° intervals from the 12 o'clock position. Variations in temperature ranged from 332° F. to 604° F., as shown in FIG. 6. Similarly, screen temperatures were measured at positions two inches left and right of the centerline and four inches vertically starting five inches from the top edge of the screen in flow path 1 of FIG. 1, and the results are shown in FIG. 6. The screen temperatures were non-uniform and exceeded 1400° F. at some locations, which is undesirable.

COMPARATIVE EXAMPLE 2

Figure 4:
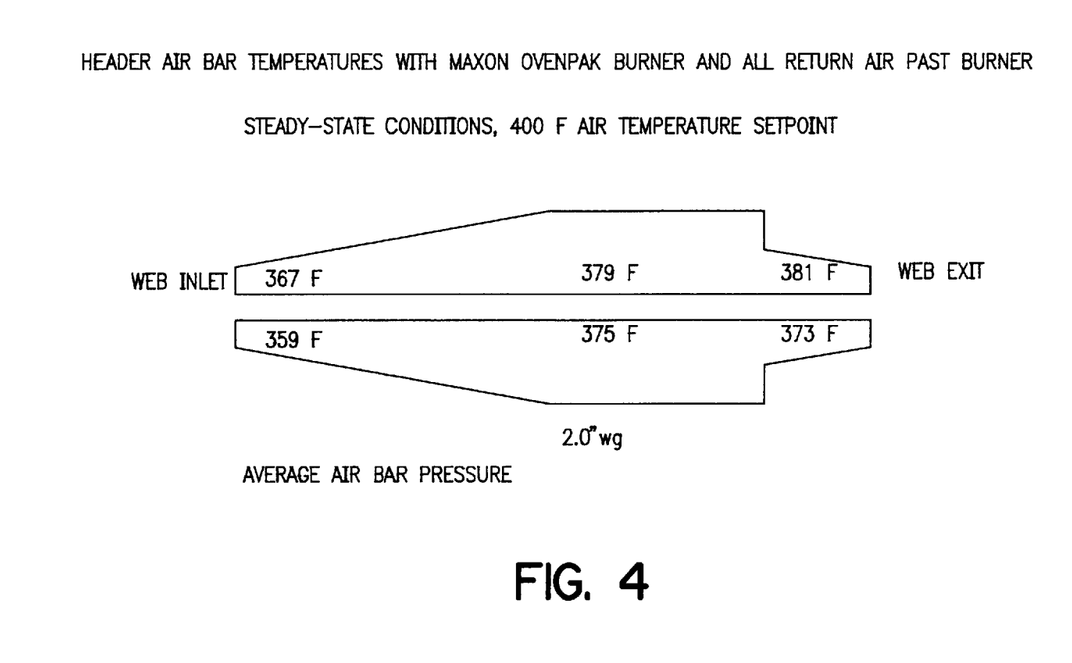
FIG. 4 is an illustration showing header air bar temperatures with all of the return air flowing past the burner.
Figure 5:
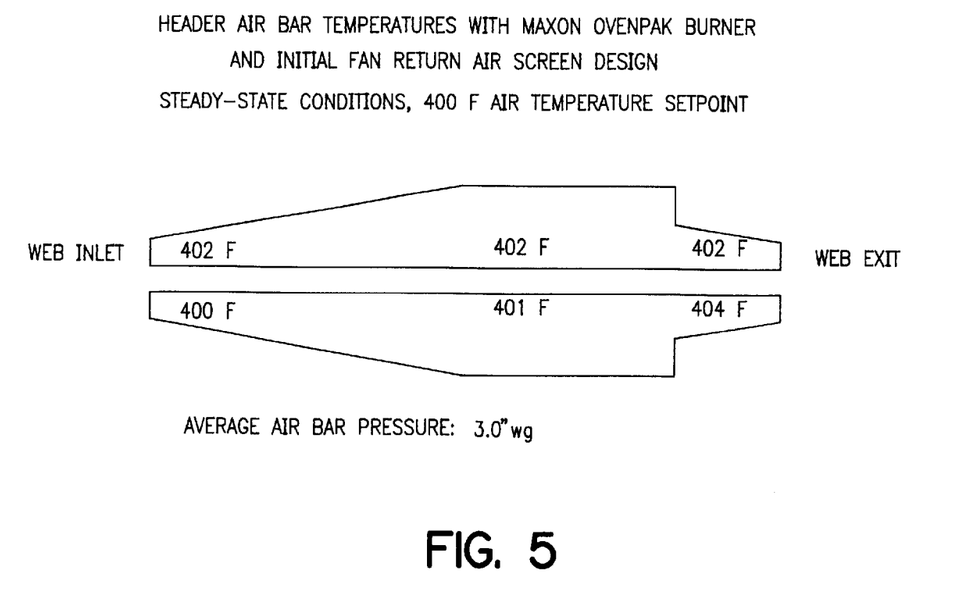
FIG. 5 is an illustration showing header air bar temperatures with a return air screen in accordance with the present invention.
Figure 7:
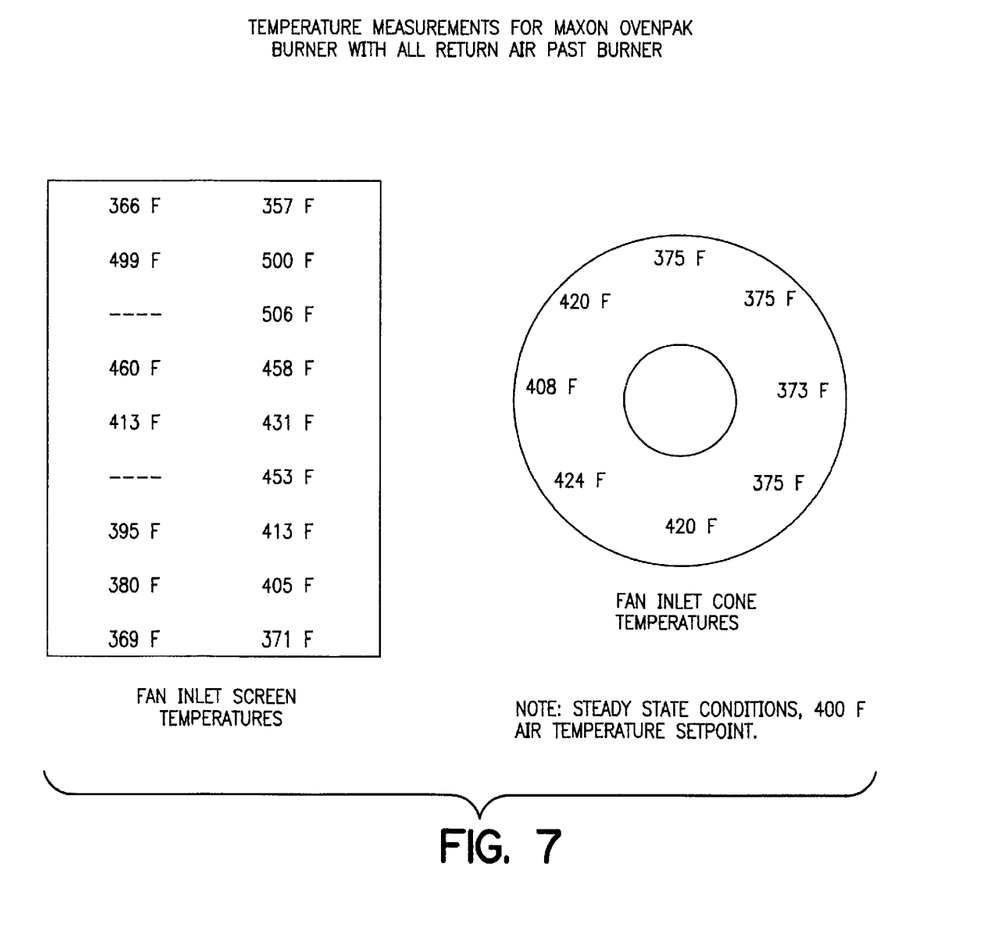
FIG. 7 is an illustration showing temperature measurements at the fan inlet screen and fan inlet cone with all return air passing by the burner.

Additional temperature measurements were carried out as in Comparative Example 1, except that the condition of 0% open area in the flow paths other than the path past the burner was maintained. FIG. 4 illustrates the non-uniformity of supply air temperature to the air bars, and FIG. 7 sets forth the results of screen temperature and fan inlet cone temperature measurements. From these results, it is seen that inlet air temperatures to the fan are much lower and more uniform. However, the average air bar pressure (FIG. 4) was only 2.0" wg, dropping from 3.1" wg. This results in an inefficient design, as the fan rpm would need to increase along with fan power to obtain the same air bar performance.

EXAMPLE 1

Figure 8:
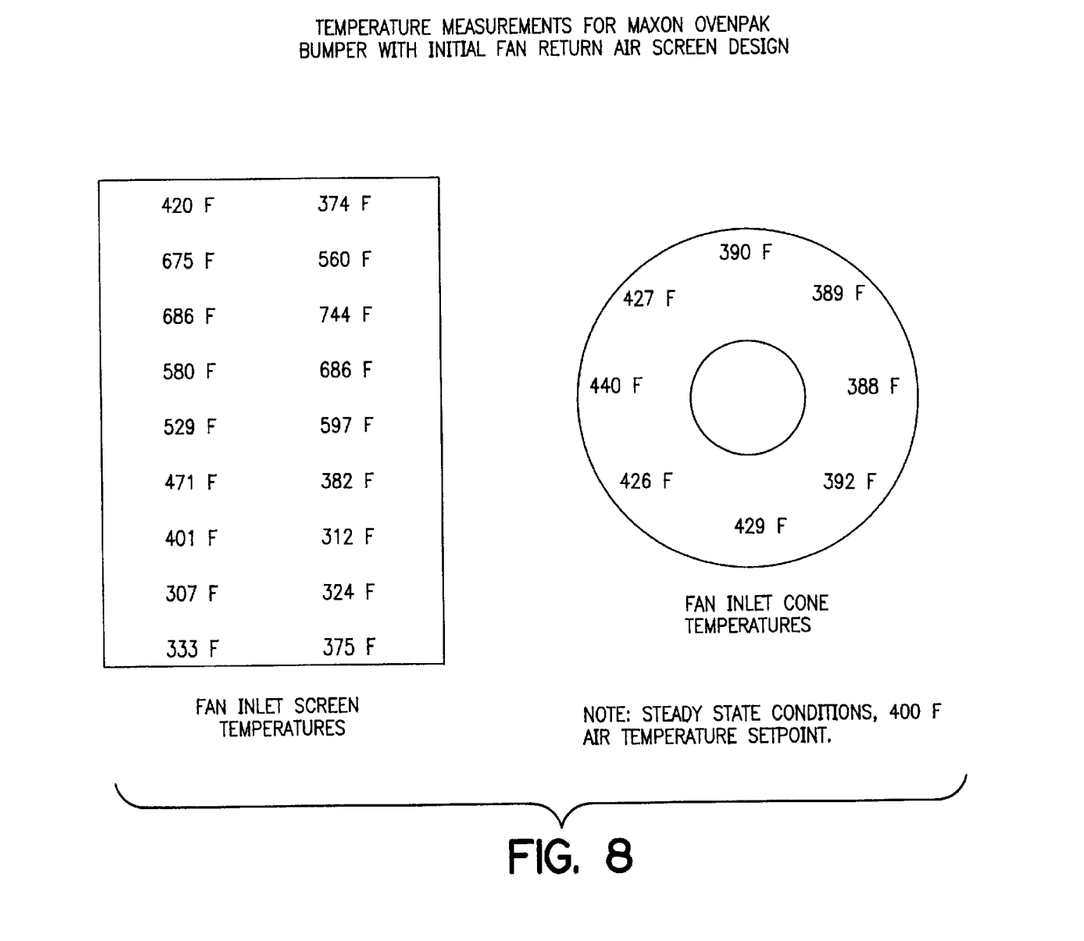
FIG. 8 is an illustration showing temperature measurements at the fan inlet screen and fan inlet cone with a return air screen in accordance with the present invention.

Air screens designed as detailed above were installed in a dryer, and the same header air bar temperature, screen temperature and fan inlet cone temperature measurements were made as in the comparative examples. The results are shown in FIGS. 4 and 8. The header air temperatures are uniform and the average air bar pressure is nearly equal to the pressure measured with no screens, 3.0" versus 3.1" wg. In FIG. 8, temperatures at the fan inlet cone only vary by 52° F., and fan inlet screen temperatures are also uniform.

What is claimed is:

1. An air flotation dryer for drying a running web in a web path, comprising:
   a dryer housing having a web inlet and a web outlet spaced from said web inlet;
   a plurality of air bars positioned in said dryer housing to floatingly support and dry said running web;
   a supply air fan having a fan inlet and a fan outlet, said fan outlet being in communication with said plurality of air bars via headers for supplying heated air to said air bars;
   a burner associated with said dryer housing for heating a portion of air entering said fan inlet; and
   air flow resistance means between said burner and said fan inlet for regulating the amount of air which is heated by said burner.

2. The dryer of claim 1, wherein said air flow resistance means comprises a return air screen having a predetermined open area.

3. The dryer of claim 1, wherein said air flow resistance means comprises a solid panel having one or more openings therein.

4. The dryer of claim 3, wherein the size of said one or more openings in said panel is adjustable.

5. The dryer of claim 2, wherein said burner fires directly into said dryer housing.

6. The dryer of claim 2, wherein said burner is a draw-through burner.

7. The dryer of claim 2, wherein said return air screen has about 10–50% open area.

8. The dryer of claim 1, wherein said burner fires directly into said dryer housing.

9. The dryer of claim 1, wherein air flow to said supply air fan comprises air from: (1) a first air flow path flowing past said burner comprising a first portion of recirculation air; and (2) a second air flow path comprising a second portion of recirculation air, and wherein said air flow resistance means is positioned in said first air flow path.

10. The dryer of claim 9, wherein said second air flow path comprises air flowing across said headers and air flow parallel to said headers.

11. The dryer of claim 1, wherein air flow to said supply air fan comprises air from: (1) a first air flow path flowing past said burner comprising a first portion of recirculation air; and (2) a second air flow path comprising a second portion of recirculation air, and wherein said air flow resistance means is positioned in said second air flow path.

12. The dryer of claim 11, wherein said second air flow path comprises air flowing across said headers and air flow parallel to said headers.

13. The dryer of claim 1, wherein air flow to said supply air fan comprises air from: (1) a first air flow path flowing past said burner comprising a first portion of recirculation air; and (2) a second air flow path comprising a second portion of recirculation air, and wherein said air flow resistance means is positioned in said first and second air flow paths.

14. The dryer of claim 1, wherein said burner is a draw-through burner.

15. An air flotation dryer for drying a running web in a web path, comprising:
- a dryer housing having a web inlet and a web outlet spaced from said web inlet;
- a plurality of air bars positioned in said dryer housing in communication with ducting;
- a supply air fan having an fan inlet and a fan outlet, said fan outlet being in communication with said plurality of air bars via said ducting for supplying heated air to said air bars to floatingly support and dry said running web;
- a burner associated with said dryer housing for heating a portion of air entering said fan inlet;
- a first air flow path to said fan flowing past said burner consisting essentially of make-up air and a first portion of air recirculating from said air bars;
- a second air flow path to said fan consisting essentially of a second portion air recirculating from said air bars, said second portion of air flowing into said fan inlet without passing past said burner; and
- air flow resistance means between said burner and said fan inlet for regulating the amount of recirculation air in said first portion of air recirculating from said air bars.

16. The dryer of claim 15, wherein said air flow resistance means comprises a return air screen in at least said first air flow path, said return air screen having a predetermined open area.

17. The dryer of claim 16, wherein said return air screen has about 10–50% open area.

18. The dryer of claim 15, wherein said air flow resistance means comprises a solid panel having one or more openings therein.

19. The dryer of claim 18, wherein the size of said one or more openings in said panel is adjustable.

20. The dryer of claim 18, wherein 10–50% of the area of said panel is open.

21. A method of controlling the amount of air heated by a burner in an air flotation dryer having a dryer housing having a web inlet and a web outlet spaced from said web inlet; a plurality of air bars positioned in said dryer housing to floatingly support and dry said running web; a supply air fan having a fan inlet and a fan outlet, said fan outlet being in communication with said plurality of air bars via headers for supplying heated air to said air bars; and a burner associated with said dryer housing for heating a portion of air entering said fan inlet; said method comprising:
- causing a predetermined portion of air to be heated by said burner prior to entering said supply fan inlet.

22. The method of claim 21, wherein air flow resistance means is positioned in said dryer housing to cause said predetermined portion of air to be heated.

23. The method of claim 22, wherein said air flow resistance means comprises a screen having a predetermined open area.

24. The method of claim 22, wherein said air flow resistance means has a variable open area.

* * * * *